(12) United States Patent
Sahiri

(10) Patent No.: US 9,952,142 B2
(45) Date of Patent: Apr. 24, 2018

(54) MEASURING HEAD WITH ILLUMINATION

(71) Applicant: Implen GmbH, Munich (DE)

(72) Inventor: Thomas Sahiri, Calabasas, CA (US)

(73) Assignee: Implen GmbH, Munich (DE)

( * ) Notice: Subject to any disclaimer, the term of this patent is extended or adjusted under 35 U.S.C. 154(b) by 0 days.

(21) Appl. No.: 15/114,376

(22) PCT Filed: Dec. 4, 2014

(86) PCT No.: PCT/EP2014/076564
§ 371 (c)(1),
(2) Date: Jul. 26, 2016

(87) PCT Pub. No.: WO2015/082611
PCT Pub. Date: Jun. 11, 2015

(65) Prior Publication Data
US 2017/0010206 A1    Jan. 12, 2017

(30) Foreign Application Priority Data

Dec. 4, 2013 (DE) .......... 10 2013 224 846

(51) Int. Cl.
*G01N 1/10* (2006.01)
*G01N 21/25* (2006.01)
(Continued)

(52) U.S. Cl.
CPC .......... *G01N 21/25* (2013.01); *G01J 3/0218* (2013.01); *G01N 21/01* (2013.01); *G01N 21/03* (2013.01); *G01N 21/0303* (2013.01); *G01N 21/11* (2013.01); *G01N 2021/035* (2013.01); *G01N 2021/0314* (2013.01);
(Continued)

(58) Field of Classification Search
CPC .......... G01J 3/0218; G01N 2021/0314; G01N 2021/035; G01N 2021/6417; G01N 2021/6482; G01N 2021/6484; G01N 21/01; G01N 21/03; G01N 21/0303;
(Continued)

(56) References Cited

U.S. PATENT DOCUMENTS 6,104,485 A    8/2000 Wang et al.
7,235,245 B2   6/2007 Jacob et al.
(Continued)

FOREIGN PATENT DOCUMENTS

WO    WO 89/02718    6/1989

OTHER PUBLICATIONS

Pena-Pereira et al. "Advances in Miniaturized UV-Vis Spectrometric Systems", Trends in Analytical Chemistry, vol. 30, No. 10, pp. 1637-1638 (2011).

*Primary Examiner* — Sunghee Y Gray
(74) *Attorney, Agent, or Firm* — Rutan & Tucker, LLP

(57) ABSTRACT

The invention relates to a device (1) for the light spectroscopic analysis of a small amount of a liquid sample, comprising a receiving point (3) for receiving small amounts of the liquid sample, and light conductors (5, 6) which guide light of a light source to the sample and guide signal light from the sample in the direction of a detector, and is characterised in that an illumination source (7) is arranged below the receiving point (3), and a region (8) below the receiving point (3) which is permeable for the light of the illumination source (7), is provided such that the illumination light illuminates the receiving point (3).

7 Claims, 2 Drawing Sheets

(51) Int. Cl.
*G01N 21/01* (2006.01)
*G01N 21/03* (2006.01)
*G01J 3/02* (2006.01)
*G01N 21/11* (2006.01)
*G01N 21/64* (2006.01)

(52) U.S. Cl.
CPC ............... *G01N 2021/6417* (2013.01); *G01N 2021/6482* (2013.01); *G01N 2021/6484* (2013.01); *G01N 2201/062* (2013.01); *G01N 2201/0633* (2013.01); *G01N 2201/08* (2013.01)

(58) Field of Classification Search
CPC .. G01N 21/11; G01N 21/25; G01N 2201/062; G01N 2201/0633
USPC ......................................................... 356/246
See application file for complete search history.

(56) References Cited

U.S. PATENT DOCUMENTS

| | | |
|---|---|---|
| 7,483,138 B2 | 1/2009 | Sahiri et al. |
| 7,688,429 B2 | 3/2010 | Sahari et al. |
| 2006/0051306 A1 | 3/2006 | Brown et al. |
| 2006/0109467 A1 | 5/2006 | Evans |
| 2007/0224087 A1 | 9/2007 | Ding |
| 2008/0106742 A1* | 5/2008 | Sahiri .................... G01N 21/59 356/440 |
| 2008/0204755 A1* | 8/2008 | Sahiri ................ G01N 21/0303 356/440 |
| 2010/0085571 A1 | 4/2010 | Robertson, Jr. et al. |

* cited by examiner

MEASURING HEAD WITH ILLUMINATION

This application is the national phase application of PCT/EP2014/076564, filed Dec. 4, 2014, which claims the benefit of German Application No. 10 2013 224 846.6, filed Dec. 4, 2013, each of which is incorporated by referene herein in its entirety.

TECHNICAL FIELD

The present invention relates to a device for the light spectroscopic analysis of a small amount of a liquid sample, light being guided through the medium and then being able to be detected or analyzed photometrically, spectrophotometrically, fluorimetrically and spectrofluorimetrically.

Such devices are known, for example, from EP 1 743 162 B1. In the device described here a drop or a very small amount (of the order of below 10 microliters) of a liquid sample is applied to an upper receiving point. The receiving point is in the form, for example, of a two-dimensional indentation and is dimensioned to correspond to the small volume of the sample, and so is relatively small. It is therefore often difficult for a user to see the receiving point accurately with the naked eye, and this often leads to the liquid sample only being partially applied to the receiving point, and part of it landing outside of the latter, and so on the one hand not being available as a volume for analysis, and on the other hand contaminating the device.

In devices such as those that are described in EP 1 210 579 B1 and in which a drop of a liquid sample is held freely, without any further restriction, between two receiving surfaces to be moved towards one another due to its surface tension, the problem also arises that the surface receiving the drop is hard to see with the naked eye.

The prior art, for example US 2006/0 051 036 A1 discloses fiber optic endoscopes which, in addition to guiding the excitation light for spectroscopic analyses, also guide white light for the imaging of fabric that is to be observed endoscopically. However, this equipment is not designed to receive very small amounts of liquid because it does not have a corresponding receiving point and so cannot illuminate a sample receiver either.

DESCRIPTION OF THE INVENTION

It is therefore the object of the present invention to further develop a generic device for the light spectroscopic analysis of a small amount of liquid sample such that the visibility of the upper two-dimensional receiving point is improved and so handling is simplified and is less prone to error. This object is achieved with the aid of a device for the light spectroscopic analysis of a small amount of liquid sample, as described herein.

The device according to the invention for the light spectroscopic analysis of a small amount of a liquid sample comprises a receiving point for the application of a small amount of the liquid sample, and light conductors which guide light of a light source to the sample and guide signal light from the sample in the direction of a detector, an illumination source being provided below the receiving point and a region being provided below the receiving point which is permeable for the light of the illumination source so that the illumination light illuminates the receiving point.

If a user now wishes to apply a small amount, for example a drop, of a liquid sample to the receiving point, the receiving point, which can be, for example, a two-dimensional indentation on the upper side of the device or of its housing, as described in EP 1 743 162 B1, or also a solid surface in the form of an anvil as disclosed in EP 1 210 579131, is illuminated from behind (below) so that the user can precisely identify the receiving point and, when applying drops, applies the sample with a higher degree of reliability within the delimitation of the receiving point so that on one hand no volume of the sample is lost, and on the other hand the upper side of the device is not contaminated. Small amounts are to be understood as sample amounts of less than 10 µl volume or 10 mg mass, and so the sample receiving point has to be correspondingly dimensioned and configured.

In this connection, the light conductors are preferably glass fibers which guide light of a light source, such as for example a xenon lamp, to the receiving point so that the light can pass through the sample a first time, is reflected by the reflector and can pass through the sample for a second time. The signal light that is produced here carries the spectroscopic signature of the sample and is guided by a light conductor away from the receiving point to a detector, for example a spectrometer.

The illumination source provided below the receiving point here is a light source in addition to the light source and which is not used for spectroscopic excitation, but in order to provide illumination for the receiving point which is suitable for the human eye. For this purpose the illumination light passes through a region directly below the receiving point, which region is permeable for the illumination light so that the latter can pass to the receiving point. Advantageously, this region extends from the illumination source to the receiving point or its lower side. Since the receiving point must be transparent for the light spectroscopic analysis in order to allow both incoming light and signal light to pass through, the illumination light can thus also pass through the receiving point and guarantee the visibility of the receiving point for the user.

Illumination is to be understood here to mean both the total illumination of the receiving point and the partial illumination, for example only of the edge of the receiving point. For better visibility of the receiving point it is furthermore conceivable for only the receiving point itself to be produced from transparent material, whereas adjacent material to the side of the receiving point e.g. on the upper side of the device or of a housing or at the sides of an anvil, on which the receiving point is located, is not optically transparent, for example is appropriately blackened.

In accordance with the invention the region that is permeable to light is located below the receiving point. This includes both regions directly vertically below the receiving point and regions that are located below but offset to the side of the receiving point. It is conceivable, for example, for there to be no regions guiding the illumination light along the vertical projection of the receiving point, for example because optical fibers guiding incident and signal light are located here, but the regions which are located to the side of the aforementioned projection are transparent, and so guide the illumination obliquely upwards to the receiving point.

Preferably, the device also comprises a reflector provided above the receiving point that can be swiveled or detached for opening and closing, in the usage position the receiving point being located on the upper side of the device. The device can optionally correspondingly also comprise a housing on the upper side of which the receiving point is located in the usage position, and on which the reflector is provided such that it can swivel or be detached.

"Usage position" is to be understood here to mean the orientation of the device in which on the one hand the liquid sample is applied or dripped onto the receiving point, but on the other hand also the preferred orientation in which the device is positioned within a spectrometer. In general this means that the, for example, elongate device or its housing, on the upper side of which the receiving point is provided and is covered with the reflector that can be swiveled or detached, is in an upright or vertical orientation. Here the reflector is preferably incorporated into a cover that can be placed or screwed on the upper side of the device or of the housing, or is attached by a hinge such as to be able to swivel, further fastening possibilities, also with the aid of fixing elements such as screws or pins, being conceivable. It is essential that the reflector, and optionally with it the lid, can be opened in order to gain access to the receiving point from above, and can be closed so that the reflector, along with the receiving point, forms a volume of sample that is filled by the sample liquid.

According to an alternative configuration it is conceivable for the receiving point to be a receiving surface, and for a moveable surface to be provided opposite the receiving surface, which moveable surface can move towards the receiving surface so that the liquid sample is inserted between the receiving surface and the moveable surface. The receiving surface can be located, for example, on the upper side of an anvil, and a light conductor can guide light through the moveable surface to the sample, while another light conductor guides the signal light through the receiving surface to the detector.

Preferably, the illumination source is a real or a virtual light source. In the case of the real illumination source there is located below the receiving point a directly light-generating source such as an incandescent lamp, an LED etc. which, for example, emits substantially white light so that the receiving point is illuminated white. If a housing is provided, the directly light-generating source is located below the receiving point within the housing.

In the case of a virtual light source, the actual light source, for example an LED, is located in a position below the receiving point, in particular in a position away from the housing, and the illumination light of the illumination source is guided with the aid of a light conductor, such as for example a glass fiber, to beneath the receiving point (e.g. into the housing), where the end of the light conductor constitutes the virtual illumination source.

Particularly preferably, the region that is permeable to light is a transparent part of the housing. For example, for this purpose the region of the housing which receives the ends of the light conductors immediately below the receiving point is made to be transparent.

It is particularly preferable here if the region that is permeable to light is a glass tube that extends from the receiving point to the illumination source. This tube therefore guides the illumination light by conducting light directly from the illumination to the receiving point.

Alternatively, the region that is permeable to light can also be a bore hole, the clear diameter of which is not entirely filled by the light conductors. Space is thus created around the light conductors through which the illumination light can pass from below to the receiving point.

In general it is preferred if the illumination source is a light emitting diode located directly beneath the receiving point (e.g. in the housing) as a real light source. If so required the light emitting diode can have a different color here, but white is generally preferred for the illumination. It is also conceivable for the light emitting diode to be able to change its color according to certain operating modes.

In a second aspect a device according to the invention is provided for the light spectroscopic analysis of a small amount of a liquid sample, comprising a receiving point for applying the liquid sample, and light conductors which guide light of a light source to the sample and guide signal light from the sample in the direction of a detector, characterized in that there is provided at the entrance of the light conductor guiding the light an illumination source which injects illumination light into this light conductor and so illuminates the receiving point. In this way the light conductor guiding the light can be used twice, once for exciting the sample in the receiving point, and on the other hand for illuminating the receiving point. Advantageously, for this purpose the illumination source is located at the entrance of the light conductor that guides the light so that its focal point at the other end of the light conductor does not coincide with that of the light source (which lies within the sample in the receiving point), so that the illumination light already diverges sufficiently at the receiving point in order to illuminate the receiving point.

Preferably, the device also comprises a reflector provided above the receiving point that can be swiveled and detached for opening and closing, in the usage position the receiving point being located on the upper side of the device. The device can optionally correspondingly also comprise a housing on the upper side of which the receiving point is located in the usage position and on which the reflector is provided such that it can swivel and be detached.

As in the first aspect, the receiving point can alternatively be a receiving surface and a moveable surface can be provided opposite the receiving surface, which moveable surface can move towards the receiving surface so that the liquid sample is inserted between the receiving surface and the moveable surface.

Particularly preferably, a fiber optic connector is provided at the entrance of the light conductor guiding the light, and the illumination source is disposed directly on the connector. In this way the illumination source, for example a light emitting diode, can be disposed in the gap between the light source (for example a xenon lamp) and the fiber connector (for example an SMA connector).

Finally, in one possible embodiment of the device the illumination source and the light source are integrated or combined. This means that with a light source in its own right, e.g. a combined halogen/deuterium lamp, both the illumination of the receiving point (for example by means of a dimmed halogen lamp) and the irradiation of the light is brought about for the analysis.

BRIEF DESCRIPTION OF THE DRAWINGS

In the following two exemplary embodiments of the present invention will be described with reference to the attached drawings.

DETAILED DESCRIPTION

Figure 1:
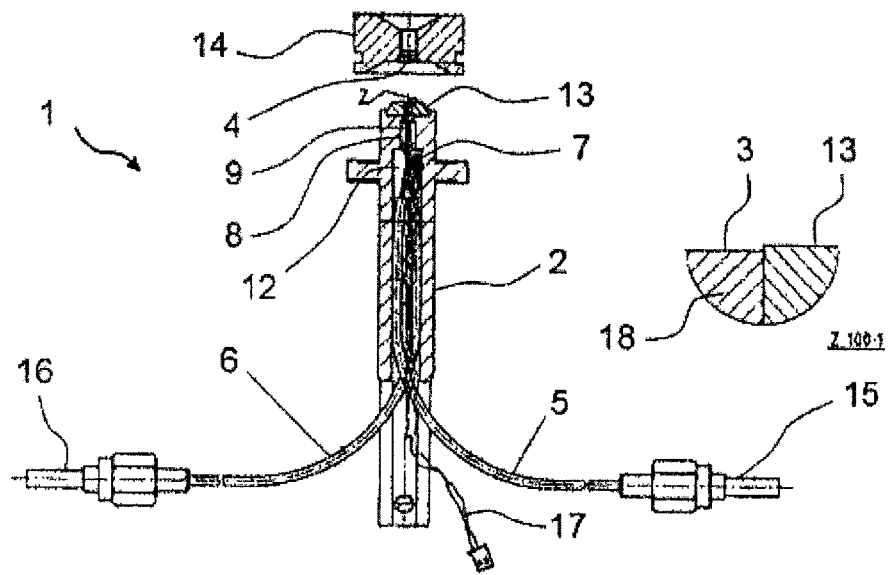
FIG. 1 shows a sectional view of a first embodiment of the device according to the invention in which a light emitting diode is provided below the receiving point.

FIG. 1 shows a sectional view of a first embodiment of the device according to the invention. The device for the light spectroscopic analysis of a small amount of a liquid sample is in this case a measuring head 1 which comprises an elongate housing 2, on the upper side of which (in the usage position, i.e. a vertical, upright orientation of the elongate housing 2) there is a sample receiver 13. The sample receiver 13 is annular in form and surrounds a receiving point 3 in the form of a two-dimensional indentation (see the enlargement indicated by "Z" in FIG. 1). The receiving point is accessible from above and allows the liquid sample to be applied, which sample is held at the receiving point 3 by the force of gravity. The bottom 18 of the receiving point 3 is formed, for example, by a material that is transparent for the excitation to signal light, such as for example quartz glass which, depending on the light guidance used, can also have lens features as described in EP 1 743 162 B1. After applying the sample the receiving point is closed from above with a cover 14 which has a reflector 4 on its lower side which terminates the receiving point from above flush with the annular sample receiver, and so forms a defined sample volume.

In order to excite the sample, light is guided to the lower side of the receiving point with the aid of a glass fiber 5 which is connected to a light source (not shown in FIG. 1) by an SMA connection 15. The light then passes through the volume of the sample, is reflected by the reflector 4, passes through the volume of the sample once again and is then guided as signal light from the glass fiber 6 to a detector which is not shown here either, for example a spectrometer, to which the fiber 6 is connected by means of an SMA connection 16. The ends of the glass fibers 5 and 6 turned towards the receiving point are adhered in a guide sleeve 9 such that the light passing out of them and into them respectively has an ideal focal point in the volume of the sample. The glass fibers 5, 6 are guided here within the inner cavity 12 of the housing 2.

Below the receiving point there is in the upper part of the cavity 12 of the housing 2 a light emitting diode 7 the power supply of which is guaranteed by means of a supply cable 17 with a corresponding plug and which is also guided through the cavity 12 of the housing 2. The light irradiated by the LED 7 can pass here through a transparent region 8, which in this instance is in the form of a glass tube 8 surrounding the guide sleeve 9, to the lower side of the receiving point 3, and so illuminate the receiving point from below. In the present exemplary embodiment the illumination light therefore passes out of the LED 7 into the glass tube 8 which guides the illumination light to the bottom 18 in the receiving point 3 and so to its lower side.

Alternatively, it is also conceivable to make the guide sleeve 9 for the optical fibers 5, 6 transparent and to use it as a transparent region for the conduction of light of the illumination light to the receiving point 3. Any scattering of the illumination light into the optical fibers 5, 6 is non-critical here because the illumination is switched off when measuring, as will be explained in more detail below.

Although it is not shown in FIG. 1, a switching mechanism can furthermore be provided which only switches on the illumination by the LED 7 when the lid 14 is removed and automatically deactivates the LED 7 after the cover 14 with the reflector 4 has been placed on the receiving point 3, i.e. it has been closed. Therefore, illumination when the cover is closed, and in particular during measurements, is switched off, and any negative impact upon the measurements is effectively prevented.

Figure 2:
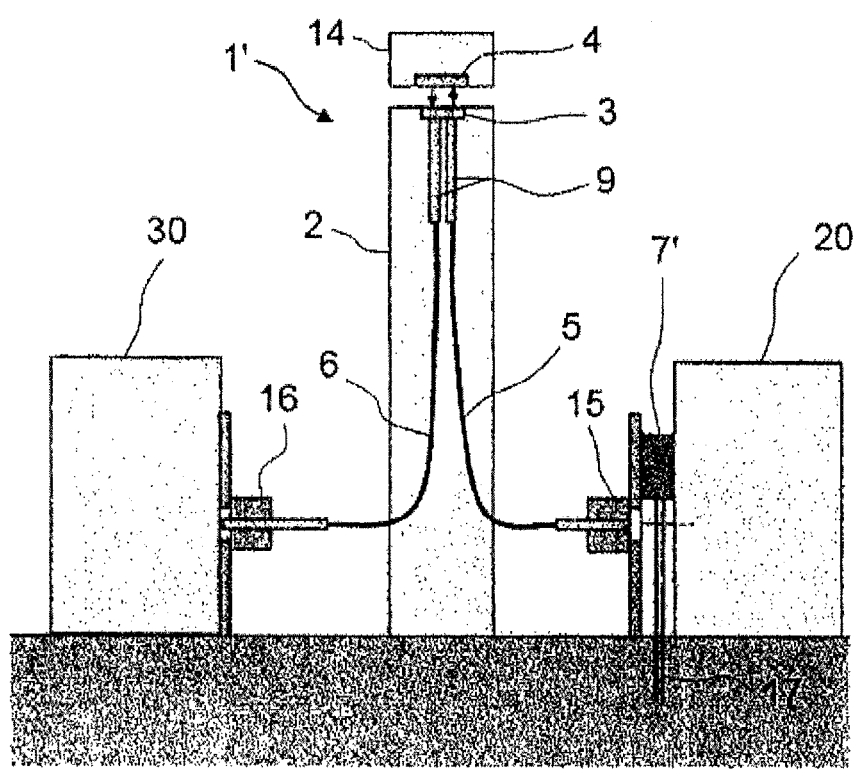
FIG. 2 shows a second embodiment of the device according to the invention in which a light emitting diode is provided on the end of the optical fiber guiding the light.

FIG. 2 shows a second embodiment of the present invention. Here the device for the light spectroscopic analysis of a small amount of a liquid sample is a measuring head 1' that substantially corresponds to the embodiment of FIG. 1. However, in this instance there is no LED below the receiving point 3, nor is there a region that is permeable to the illumination light as in the first embodiment. Instead, in this instance a light emitting diode or a halogen lamp 7' is disposed, as an illumination source, between a fiber optic connector 15 of the optical fiber 5 guiding the light to the receiving point and a xenon lamp 20 which constitutes the light source, and is connected by a power supply line 17. The light of the LED 7' is injected here into the optical fiber 5 and is guided to the receiving point 3. In this connection the light of the LED or the halogen lamp 7' is injected such that the focal point of the illumination lies within it at the other end of the fiber 5 outside of the receiving point 3 or of the sample volume so that the illumination light beam diverges sufficiently at the receiving point 3 in order to illuminate the receiving point 3.

As in the first embodiment, when measuring, i.e. when the lid 14 is in place, the LED 7' is switched off so that there is no negative impact either upon the excitation light or upon the signal light which is injected via an SMA connection 16 through the glass fiber 6 into the spectrometer (detector) 30.

The invention claimed is:

1. A device for the light spectroscopic analysis of a small amount of a liquid sample, comprising:
   a receiving point which is dimensioned and configured for receiving the small amount of the liquid sample of less than 10 μl volume or 10 mg mass;
   light conductors which guide excitation light from a light source to the sample to excite the sample and guide signal light from the sample to a detector; and
   an illumination source, which is separate from the light source and which is not used for spectroscopic excitation, is provided below the receiving point, and a region is provided below the receiving point, which is permeable to light from the illumination source and configured to provide a different optical path than the excitation light so that the illumination source illuminates the receiving point properly for a human eye.

2. The device according to claim 1, further comprising: a reflector provided above the receiving point that can be swiveled or detached to make accessible the receiving point, in a usage position the receiving point being located on an upper side of an device.

3. The device according to claim 1, the receiving point being a receiving surface, and a moveable surface being provided opposite the receiving surface, wherein the moveable surface can move towards the receiving surface so that the liquid sample is inserted between the receiving surface and the moveable surface.

4. The device according to claim 1, the illumination source being a real or a virtual light source.

5. The device according to claim 1, the region that is permeable to light being a glass tube that extends from the receiving point to the illumination source.

6. The device according to claim 1, the region that is permeable to light being a bore hole, a clear diameter of which is not entirely filled by the light conductors.

7. The device according to claim 1, the illumination source being a light emitting diode.

* * * * *